(12) United States Patent
Kamata et al.

(10) Patent No.: US 8,365,774 B2
(45) Date of Patent: Feb. 5, 2013

(54) METHOD FOR REPAIRING FLEXIBLE TUBE (75) Inventors: Kouichi Kamata, Saitama (JP); Atsushi Iwasaki, Saitama (JP); Daisuke Ayame, Saitama (JP); Nobuharu Takahashi, Saitama (JP)

(73) Assignee: Fujifilm Corporation, Tokyo (JP)

( * ) Notice: Subject to any disclaimer, the term of this patent is extended or adjusted under 35 U.S.C. 154(b) by 553 days.

(21) Appl. No.: 12/457,903

(22) Filed: Jun. 24, 2009

(65) Prior Publication Data
US 2010/0000621 A1    Jan. 7, 2010

(30) Foreign Application Priority Data
Jun. 27, 2008    (JP) .................................. 2008-168599

(51) Int. Cl.
*F16L 55/16*    (2006.01)
(52) U.S. Cl. ..................... 138/99; 264/36.16; 264/342 R
(58) Field of Classification Search ............... 138/99; 264/36.16, 342 R
See application file for complete search history.

(56) References Cited

U.S. PATENT DOCUMENTS

| | | | | |
|---|---|---|---|---|
| 3,731,710 A | * | 5/1973 | Bauer et al. .................... 138/143 |
| 4,153,747 A | * | 5/1979 | Young et al. ................. 428/41.5 |
| 4,732,412 A | * | 3/1988 | van der Linden et al. ...... 285/47 |
| 4,756,337 A | * | 7/1988 | Settineri ........................ 138/99 |
| 4,885,194 A | * | 12/1989 | Tight et al. .................... 428/34.9 |
| 4,896,904 A | * | 1/1990 | Gadsden et al. ........... 285/381.5 |
| 4,900,596 A | * | 2/1990 | Peacock ....................... 428/34.5 |
| 5,397,615 A | * | 3/1995 | Van Beersel et al. ........... 428/57 |
| 5,482,087 A | * | 1/1996 | Overbergh et al. ............ 138/110 |
| 5,632,307 A | * | 5/1997 | Fawley et al. ................... 138/99 |
| 5,662,974 A | * | 9/1997 | Andrenacci et al. ......... 428/36.9 |
| 6,355,318 B1 | * | 3/2002 | Tailor et al. .................. 428/34.9 |
| 7,938,146 B2 | * | 5/2011 | Brooks et al. ................... 138/99 |
| 2005/0203337 A1 | | 9/2005 | Matsumoto et al. |
| 2009/0038738 A1 | | 2/2009 | Nakamura |

FOREIGN PATENT DOCUMENTS

| | | |
|---|---|---|
| JP | 7-275368 A | 10/1995 |
| JP | 2002-125916 A | 5/2002 |
| JP | 2005-253950 | 9/2005 |
| JP | 2006-218107 | 8/2006 |
| JP | 2006-247262 A | 9/2006 |

OTHER PUBLICATIONS

Notification of Reason(s) for Refusal dated Sep. 5, 2012, with English translation.

* cited by examiner

*Primary Examiner* — James Hook
(74) *Attorney, Agent, or Firm* — McGinn IP Law Group, PLLC (57) ABSTRACT

Around a damaged area of a jacket of a flexible tube, a top coat layer whose adhesion to a polymer layer is weak is peeled off with an adhesive tape. The damaged area and its immediate surrounding area are sanded, and then wiped with ethanol for cleaning. A main agent and a hardening agent are heated and defoamed while being mixed to prepare a repair material. The repair material is applied to the damaged area and the immediate surrounding area. A heat shrink tube is opened along slits in an end portion and covers the flexible tube. The heat shrink tube is shrunk with hot air, pressing the repair material and making it flush with a surface of the jacket. The flexible tube is heated with an electric hot plate to harden the repair material. Thereafter, the heat shrink tube is peeled off from the flexible tube.

14 Claims, 9 Drawing Sheets

METHOD FOR REPAIRING FLEXIBLE TUBE

FIELD OF THE INVENTION

The present invention relates to a method for repairing a flexible tube. More specifically, the present invention relates to a method for repairing a damaged area on a jacket of a flexible tube used in, for example, an endoscope.

BACKGROUND OF THE INVENTION

A medical endoscope for observing a body cavity of a patient is known. A flexible tube that is an essential part of an insert section of an endoscope is constructed of a flexible tube structure around which a jacket is formed. This jacket is formed with a thermoplastic layer such as a urethane polymer layer applied to a circumferential surface of the flexible tube structure, and a top coat layer applied to the thermoplastic layer. The flexible tube structure includes a spiral tube and a tube-like mesh. The spiral tube is made of a metal band wound in a helical fashion, and the tube-like mesh wraps around the spiral tube.

The flexible tube is frequently bent or twisted during operation, and then cleaned, sterilized and disinfected after every use. Such handling causes abrasion and scratches on the jacket, which may be developed into a damaged area such as a hollow.

A repairing method in which plasma is irradiated to a damaged area of a flexible tube is known (see Japanese Patent Laid-Open Publication No. 2006-218107). This plasma irradiation removes deposits from a surface of the damaged area, and makes reactive groups project from the surface and roughens the surface so as to improve adhesion between the damaged area and the repair material applied thereto. In addition, a repairing method to put a flexible tube in an infrared heating element is known (see U.S. Patent Application Publication No. 2005/0203337 A1 corresponding to Japanese Patent Laid-Open Publication No. 2005-253950). In this method, after polymer as a repair material is applied to a damaged area, the flexible tube is put in the infrared heating element to dry and harden the repair material.

In the methods described in the above publications, No. 2006-218107 and No. 2005/0203337 A1, the repair material may be projected like edges from the surface of the top coat layer and hardened, resulting in surface irregularities of the top coat layer. After the endoscope is cleaned, disinfected and sterilized, the surface of the repaired endoscope is wiped with alcohol-soaked gauze repeatedly. During the wiping, the gauze may be snagged on the edges. A force to pull the snagged gauze may cause the repair material to peel off. This may mislead a cleaning operator to think of the repaired area as a defect.

SUMMARY OF THE INVENTION

In view of the foregoing, an object of the present invention is to provide a method for repairing a flexible tube that prevents surface irregularities caused by a repair material.

In order to achieve the above and other objects, a method for repairing a damaged area in a jacket of a flexible tube according to the present invention includes a repair material applying step, a repair tube covering step, a repair material hardening step, and a tube peeling step. In the repair material applying step, a liquid repair material is applied to the damaged area of the flexible tube. In the repair tube covering step, the damaged area is covered with a repair tube and a surface of the applied repair material is made flush with a surface of the jacket. In the repair material hardening step, the repair material is hardened. In the tube peeling step, the repair tube is peeled off from the flexible tube.

It is preferred that the repair tube is made from a material that is nonadhesive to the hardened repair material. It is preferred that the repair tube is a heat shrink tube that shrinks when heated. It is preferred that an inner diameter of the heat shrink tube before shrinking is slightly larger than an outer diameter of the jacket, and an inner diameter of the heat shrink tube after shrinking is smaller than the outer diameter of the jacket. In the repair tube covering step, the heat shrink tube is heated and heat-shrunk after covering the damaged area.

In the repair material hardening step, it is preferred that the repair material is heated at a temperature lower than a melting point of the jacket. It is preferred that the jacket at least has an inner layer and an outer layer. It is preferred that the repair material contains the same component contained in the outer layer. It is preferred that the repair material contains a component adhesive to the jacket.

It is preferred that a slit is formed in each of end portions of the repair tube.

According to the method for repairing the flexible tube of present invention, the repair material is applied to the damaged area and then the damaged area is covered with the repair tube to make the surface of the repair material flush with the surface of the jacket, and thereafter the repair material is hardened. As a result, surface irregularities of the repaired flexible tube are prevented.

BRIEF DESCRIPTION OF THE DRAWINGS

The above objects and advantages of the present invention will become more apparent from the following detailed description when read in connection with the accompanying drawings, in which.

DESCRIPTION OF THE PREFERRED EMBODIMENTS

Figure 1:
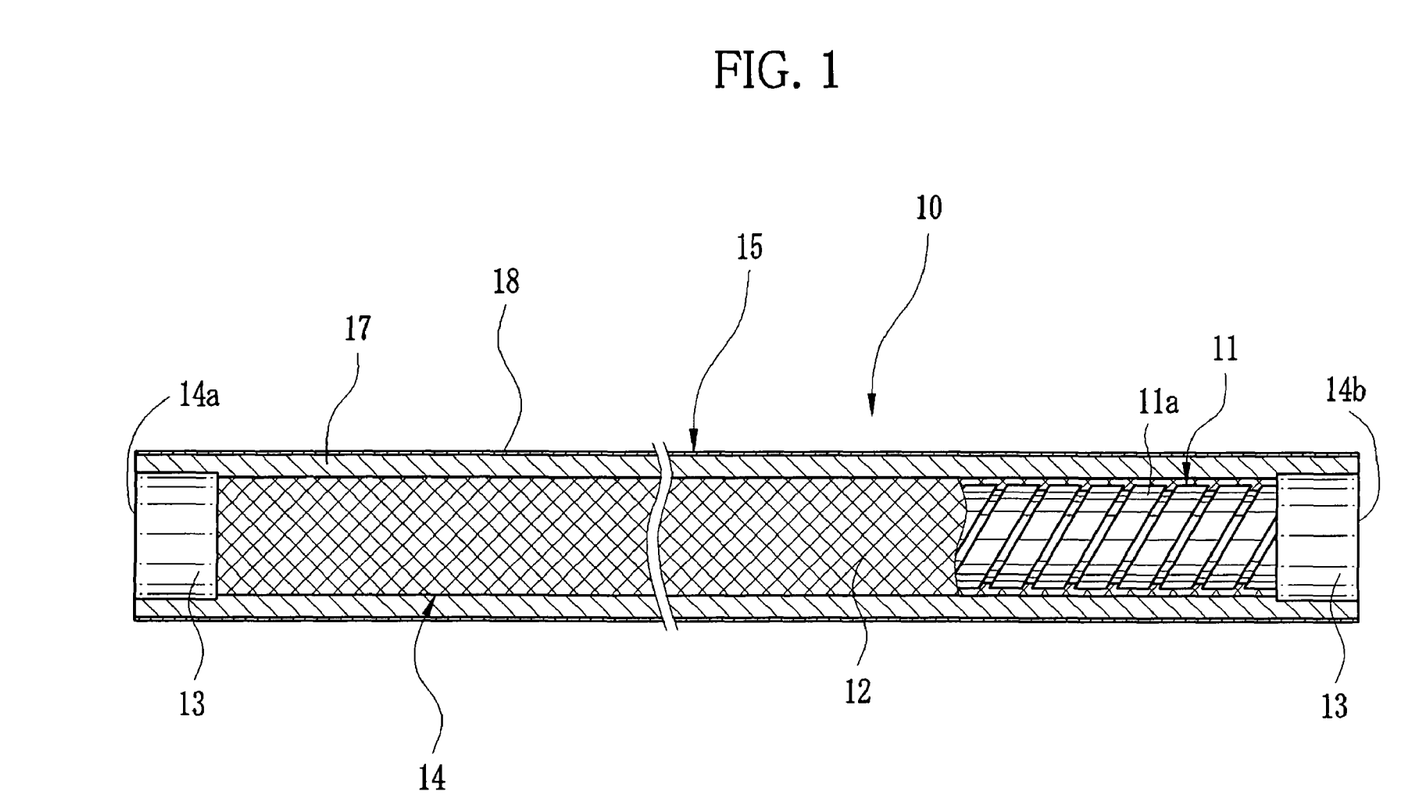
FIG. 1 is a schematic drawing of a flexible tube.

In FIG. 1, a flexible tube 10 is constructed of a flexible tube structure 14 and a jacket 15 formed on a circumferential surface of the flexible tube structure 14. The flexible tube structure 14 includes a spiral tube 11, a tube-like mesh 12, and a pair of end rings 13. The spiral tube 11 is a metal band 11a wound in a helical fashion. The tube-like mesh 12 is a braided metal wire wrapping around the spiral tube 11. The pair of end rings 13 retains the spiral tube 11 and the tube-like mesh 12. Numerals 14a and 14b indicate openings of the flexible tube 10.

The jacket 15 includes a polymer layer 17 and a top coat layer 18. The polymer layer 17 is formed on the circumferential surface of the flexible tube structure 14. The top coat layer 18 is formed on the polymer layer 17. The top coat layer 18 contains, for example, acrylic polyol as a main component. The polymer layer 17 is made of thermoplastic elastomer.

Figure 2:
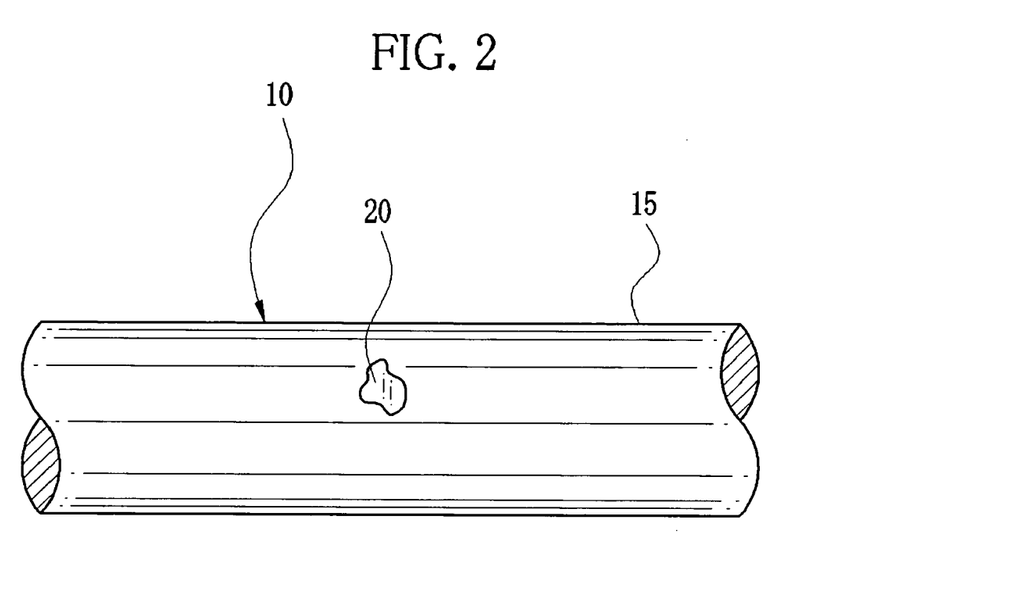
FIG. 2 is an explanatory view of the flexible tube with a damaged area on a jacket thereof.
Figure 3:
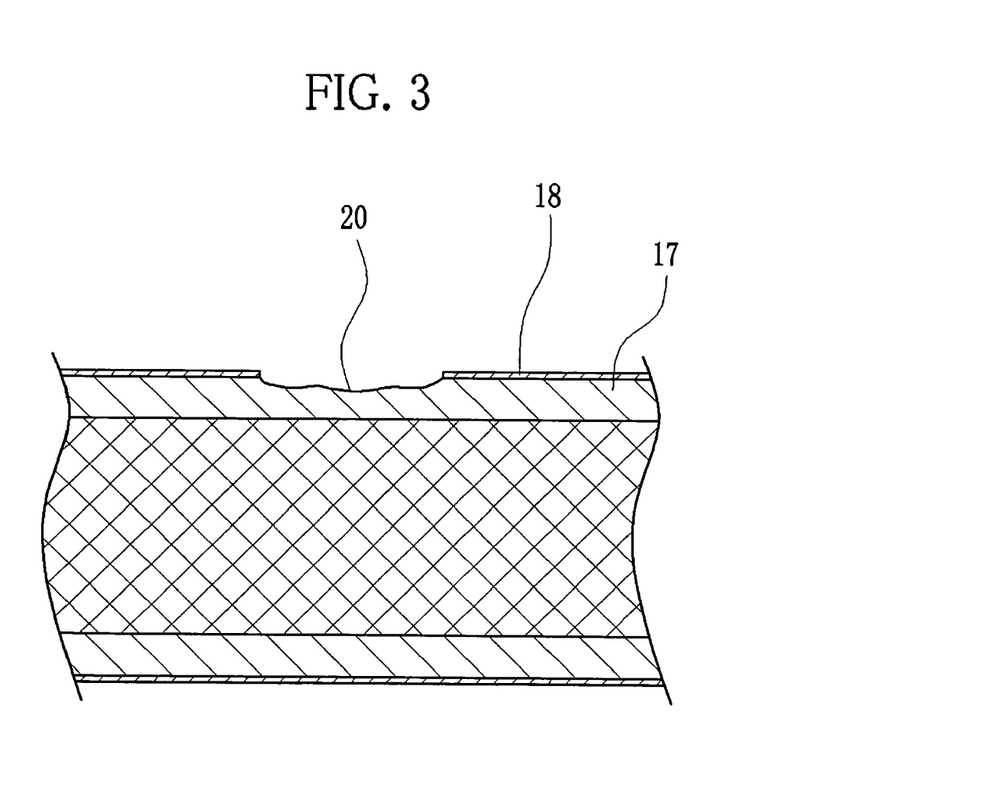
FIG. 3 is a cross-sectional view of the flexible tube with the damaged area.

The flexible tube 10 is an essential part of an insert section of an endoscope. The flexible tube 10 is bent and twisted during use, and cleaned, disinfected and sterilized after every use. After an extended period of use, a damaged area 20 may appear on a surface of the jacket 15 of the flexible tube 10 as shown in FIGS. 2 and 3. In the damaged area 20, a part of the top coat layer 18 is peeled off, and a part of the polymer layer 17 below the top coat layer 18 is also chipped, for example.

Figure 4:
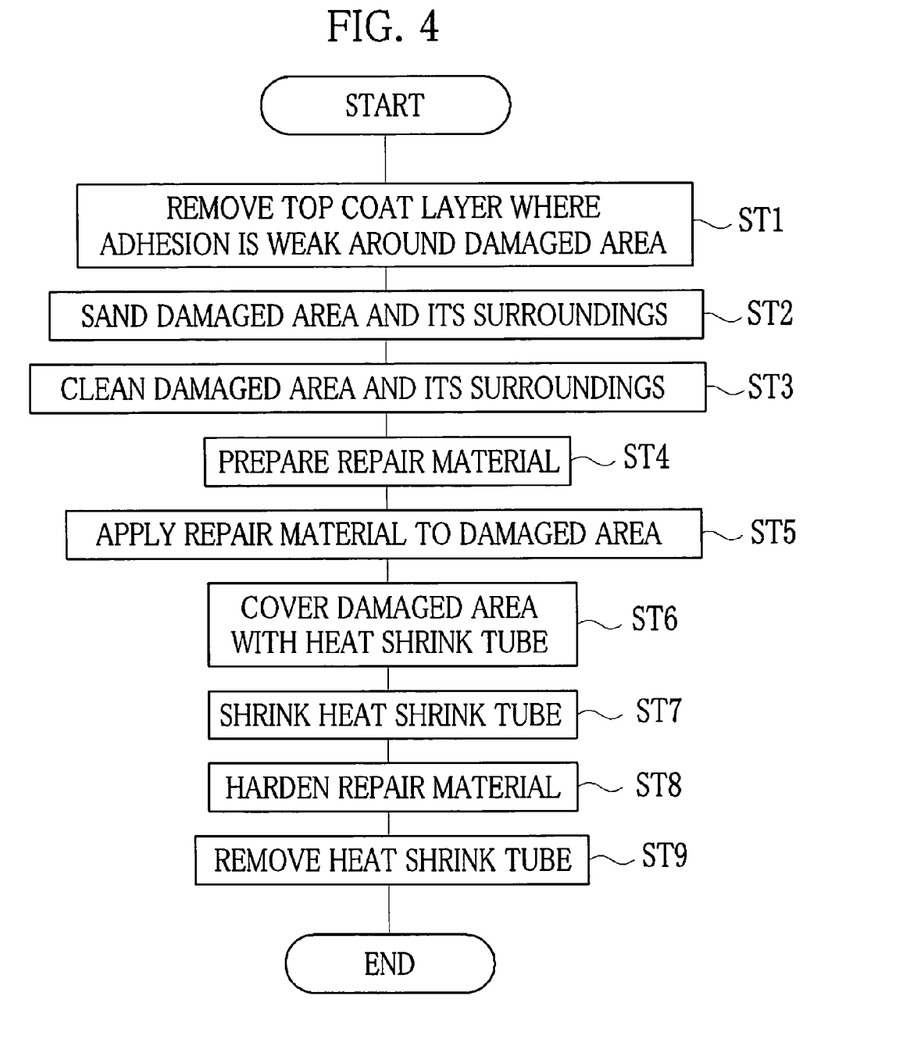
FIG. 4 is a flowchart showing a repairing method of the present invention.
Figure 5:
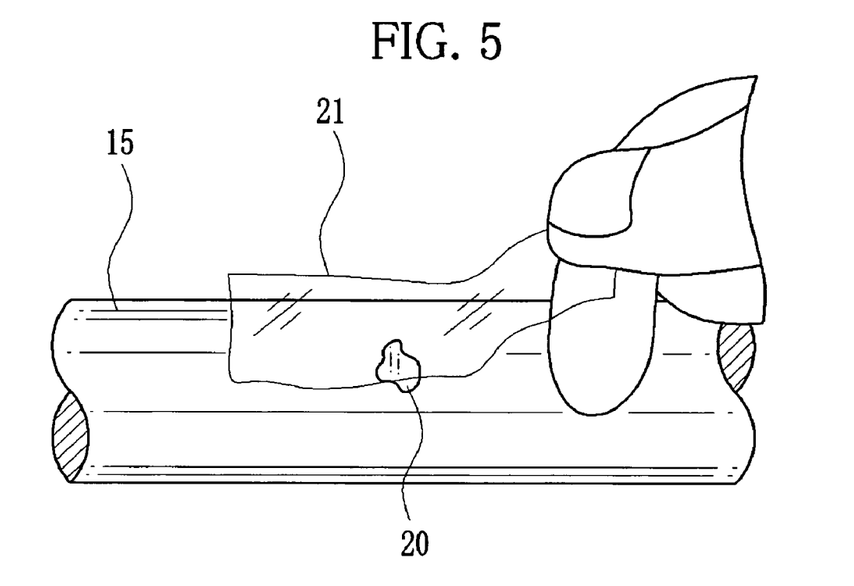
FIG. 5 is an explanatory view showing that a top coat layer is peeled off with an adhesive tape.
Figure 6:
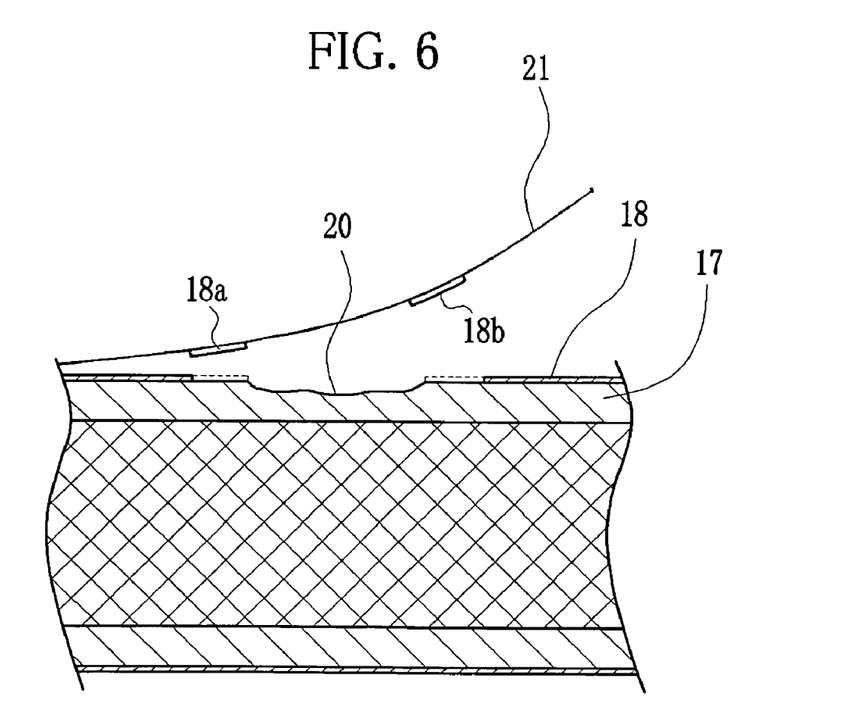
FIG. 6 is a cross-sectional view of the flexible tube showing that a part of the top coat layer is peeled off with the adhesive tape.

Next, with reference to FIGS. 4 to 14, a method for repairing the damaged area 20 is described. In a step ST1 shown in FIG. 4, portions 18a and 18b of the top coat layer 18 around the damaged area 20, where adhesion with the polymer layer 17 directly below the top coat layer 18 is weak, are peeled off using an adhesive tape 21 such as an adhesive cellophane tape as shown in FIGS. 5 and 6.

Figure 7:
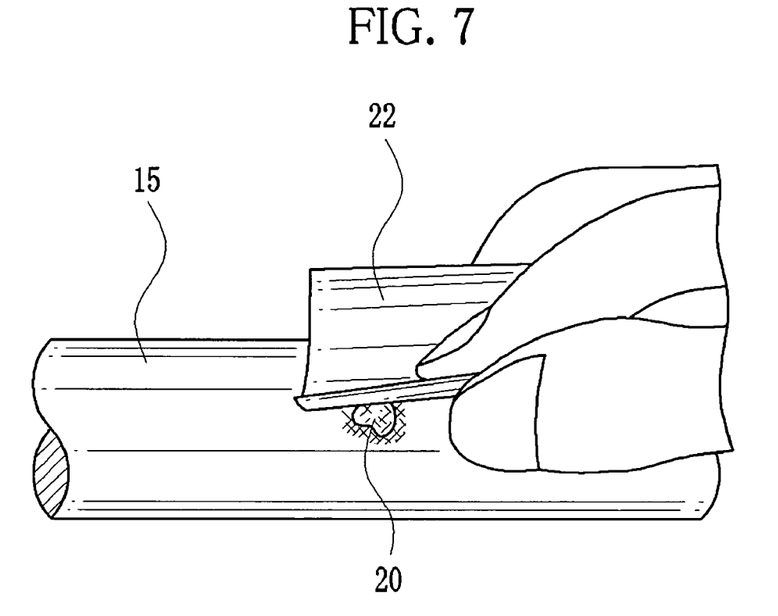
FIG. 7 is an explanatory view showing that the damaged area and its immediate surrounding area are being sanded.
Figure 8:
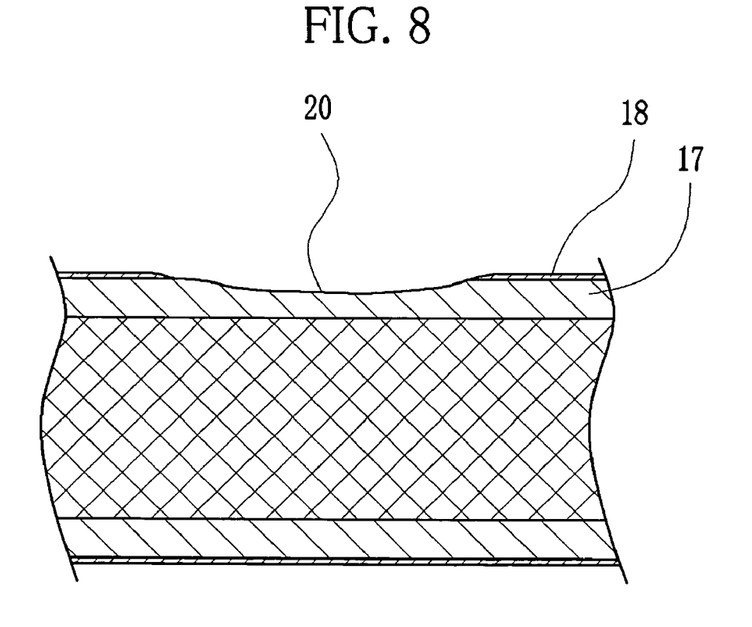
FIG. 8 is a cross-sectional view of the flexible tube with the sanded damaged area.

Then, in a step ST2, as shown in FIGS. 7 and 8, the exposed polymer layer 17 of the damaged area 20, and its immediate surrounding area, that is, a surface of the top coat layer 18 within approximately 2 mm from an edge of the damaged area 20, are sanded into a gradual concave surface using sandpaper 22. Curling up of the top coat layer 18 around the damaged area 20 is visually inspected. If there is a curled-up portion of the top coat layer 18, it is peeled off using the adhesive tape 21. Thereafter, the sanded damaged area 20 and the sanded immediate surrounding area are wiped with ethanol or the like for cleaning (ST3 in FIG. 4).

Thereafter, a repair material 23 (see FIG. 10) is prepared (ST4 in FIG. 4). The repair material 23 is a liquid. In view of adhesion with the top coat layer 18, it is preferred that a main agent of the repair material 23 is the same as a main component of the top coat layer 18, in this case, acrylic polyol. Polyisocyanate is used as a hardening agent of the repair material 23. It is preferred to record lot numbers of the main agent and the hardening agent in repair history of the flexible tube 10 to keep track of the repair material 23 used.

Figure 9:
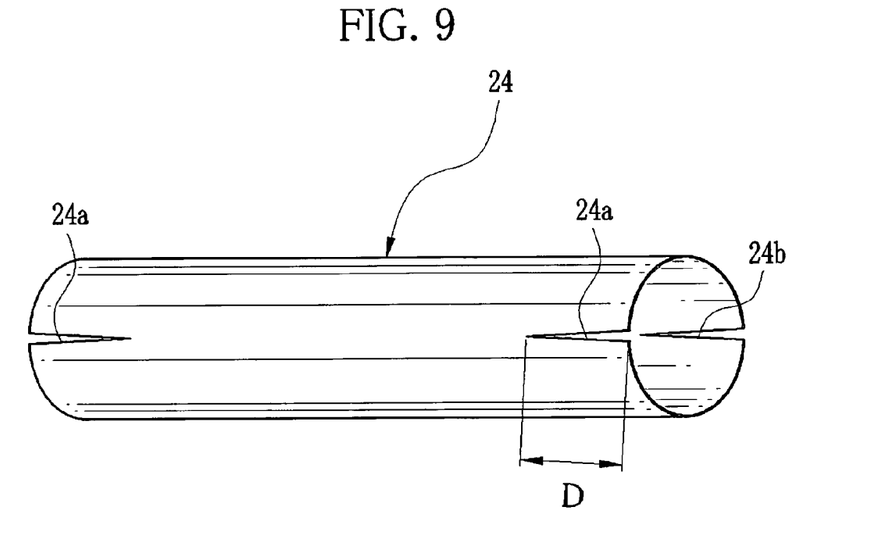
FIG. 9 is a perspective view of a heat shrink tube with a pair of slits formed in each end portion.

As shown in FIG. 9, a heat shrink tube 24 of approximately 50 mm in length is used. Before heating, namely, before shrinking, the heat shrink tube 24 has an inner diameter slightly larger than an outer diameter of the flexible tube 10. When heated, the heat shrink tube 24 shrinks and the inner diameter thereof becomes smaller than the outer diameter of the flexible tube 10. It is preferred that the inner diameter of the heat shrink tube 24 shrinks down to 70%-95% of the outer diameter of the flexible tube 10. A pair of slits 24a and 24b is formed in each end portion of the heat shrink tube 24 at positions dividing the perimeter of the heat shrink tube 24 into two equal halves. Thus, the end portions of the heat shrink tube 24 are opened widely along the slits 24a and 24b. In other words, an inner diameter of each end portion is increased. As a result, it becomes easy to insert the flexible tube 10 into the heat shrink tube 24.

For example, to cover the flexible tube 10 of 12.1 mm in outer diameter with the heat shrink tube 24 of approximately 50 mm in length and 14.5 mm in inner diameter before shrinking, a length D of each of the slits 24a and 24b is formed approximately 5 mm. The length of the heat shrink tube 24 is not limited to 50 mm. The length of the heat shrink tube 24 may be approximately 5 times as long as the length of an area where the repair material 23 is applied.

The heat shrink tube 24 is made from polyolefin that is nonadhesive to the repair material 23. Therefore, after the repair material 23 is hardened, the heat shrink tube 24 is easily peeled off from the repair material 23 and the jacket 15. The heat shrink tube 24 made from polyolefin shrinks when hot air of 110° C. or more is blown thereon for 10 to 20 seconds. Alternatively, the heat shrink tube 24 may be made from fluorine-containing polymer. In this case, the heat shrink tube 24 shrinks when hot air of 130° C. or more is blown thereon for 10 to 20 seconds.

After the slits 24a and 24b are formed in the end portions of the heat shrink tube 24, the inside of the heat shrink tube 24 is cleaned by blowing dust off with jet air, for example.

Figure 10:
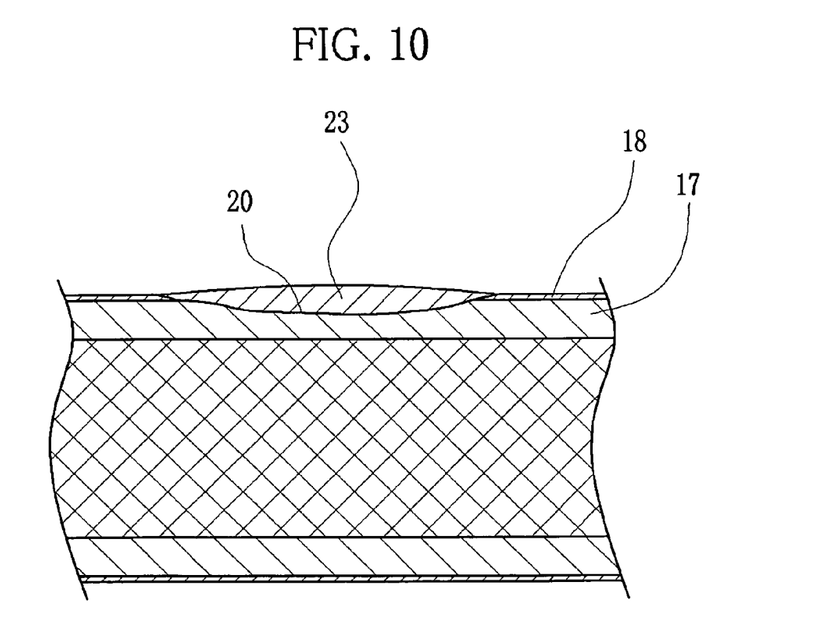
FIG. 10 is a cross-sectional view of the flexible tube with a repair material applied to the damaged area and the immediate surrounding area.

Thereafter, an appropriate amount of the repair material 23 is applied to the damaged area 20 and the immediate surrounding area as shown in FIG. 10 (ST5 in FIG. 4).

Figure 11:
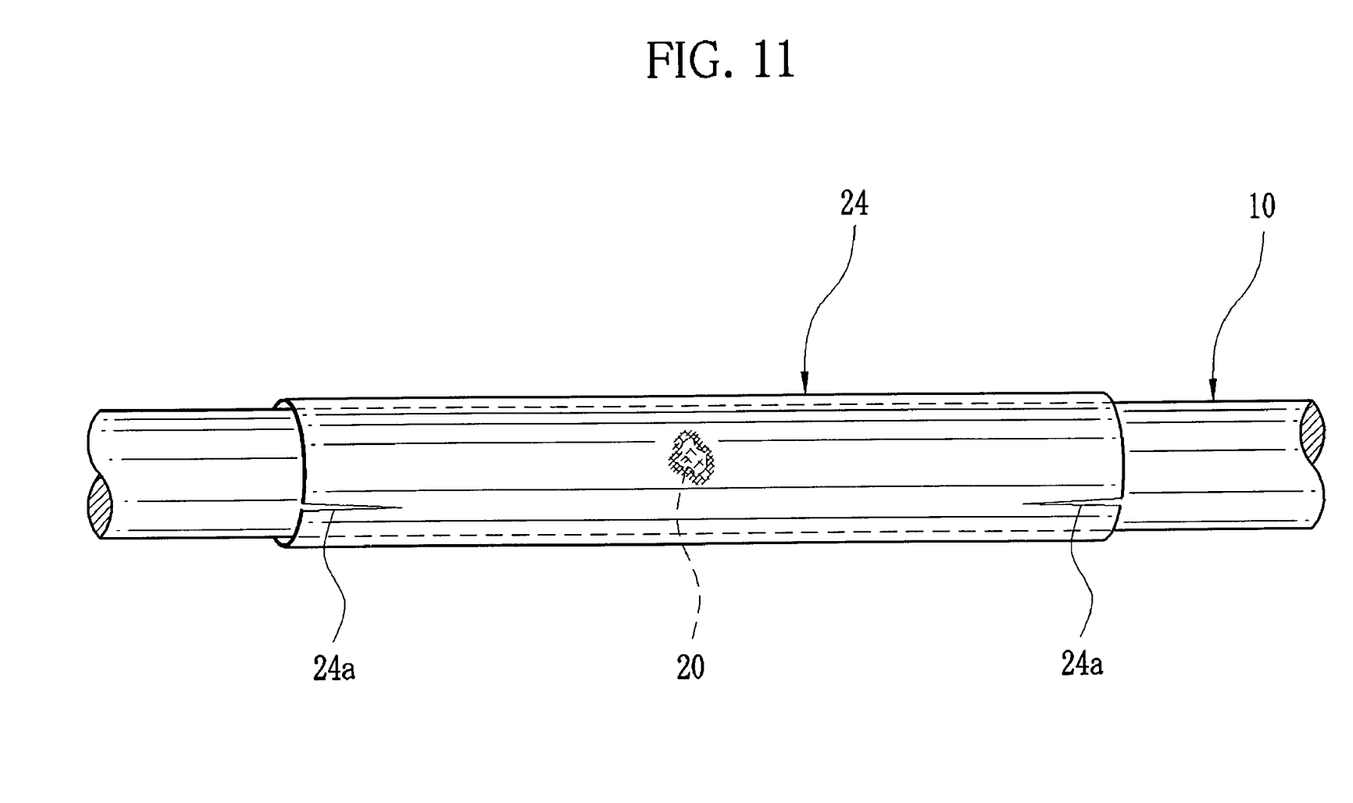
FIG. 11 is an explanatory view of the flexible tube covered with the heat shrink tube.

Next, the end portion of the heat shrink tube 24 is opened along the slits 24a and 24b to cover the flexible tube 10 such that the damaged area 20 is situated approximately at the center of the heat shrink tube 24 as shown in FIG. 11 (ST6 in FIG. 4). Caution should be taken not to contact the inner surface of the heat shrink tube 24 with the repair material 23 applied to the damaged area 20 and the immediate surrounding area.

Figure 12:
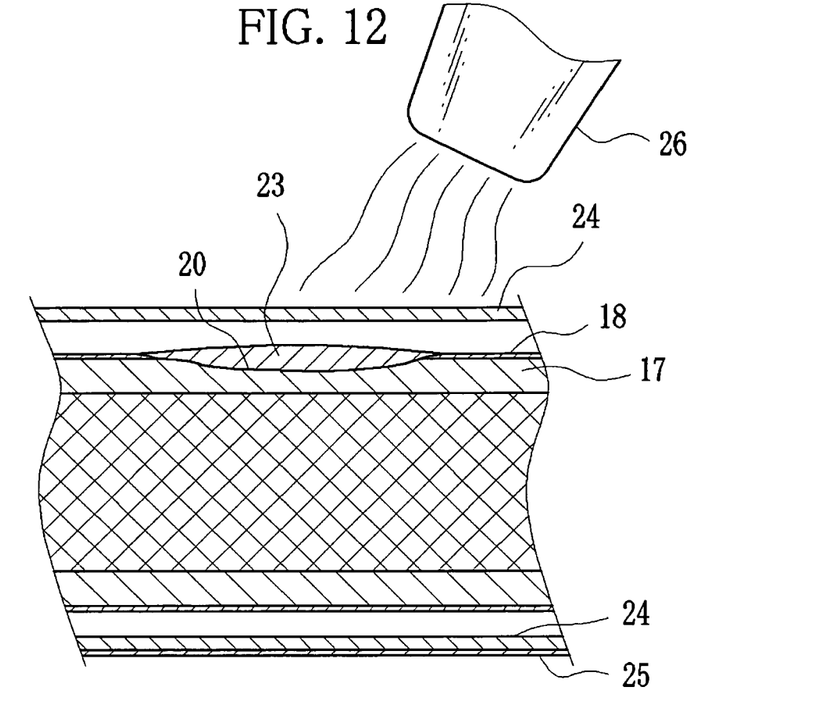
FIG. 12 is a cross-sectional view of the flexible tube covered with the heat shrink tube being blown with hot air.
Figure 13:
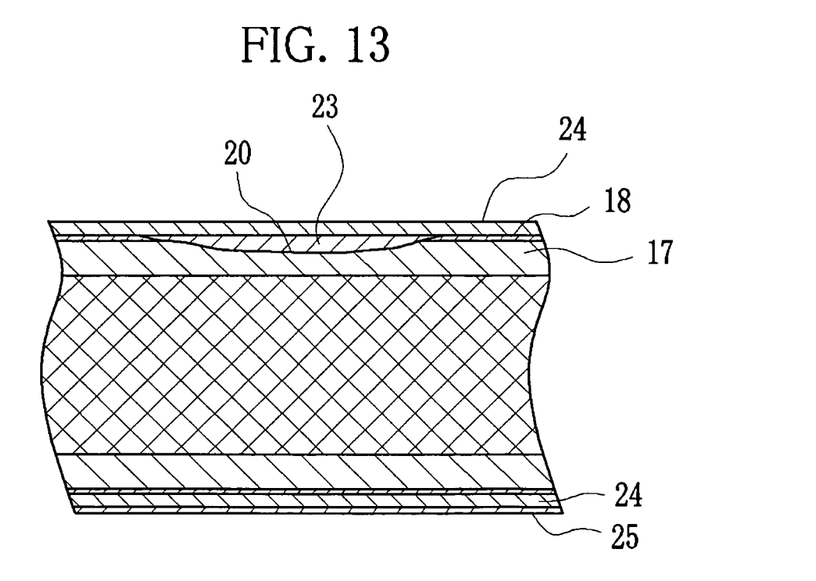
FIG. 13 is a cross-sectional view of the flexible tube covered with the heat shrink tube being shrunk down.

As shown in FIG. 12, the heat shrink tube 24 is heated with hot air at approximately 130° C. from a hot air gun 26 for 10 to 20 seconds, and shrunk as shown in FIG. 13 (ST7 in FIG. 4). Caution should be taken not to generate foam at an interface between the repair material 23 and the heat shrink tube 24.

Thereby, the inner surface of the heat shrink tube 24 presses the repair material 23 to make the surface of the repair material 23 flush with the surface of the jacket 15. The temperature of the hot air is set at approximately 130° C. so as to shrink the heat shrink tube 24 in a short time. Since the heat shrink tube 24 contains polyolefin as the main component, the temperature of the hot air may be 110° C. or above in a range that the jacket 15 is not melted.

Then, the flexible tube 10 is placed on an electric hot plate (not shown) and remained heated for approximately 12 hours at a temperature in a range from 50° C. to 70° C., that is, the temperature lower than the melting point of the jacket 15. Thus, the repair material 23 is completely hardened (ST8 in FIG. 4). Thereafter, the heat shrink tube 24 is peeled off from the jacket 15 and the repair material 23 (ST9 in FIG. 4).

Figure 14:
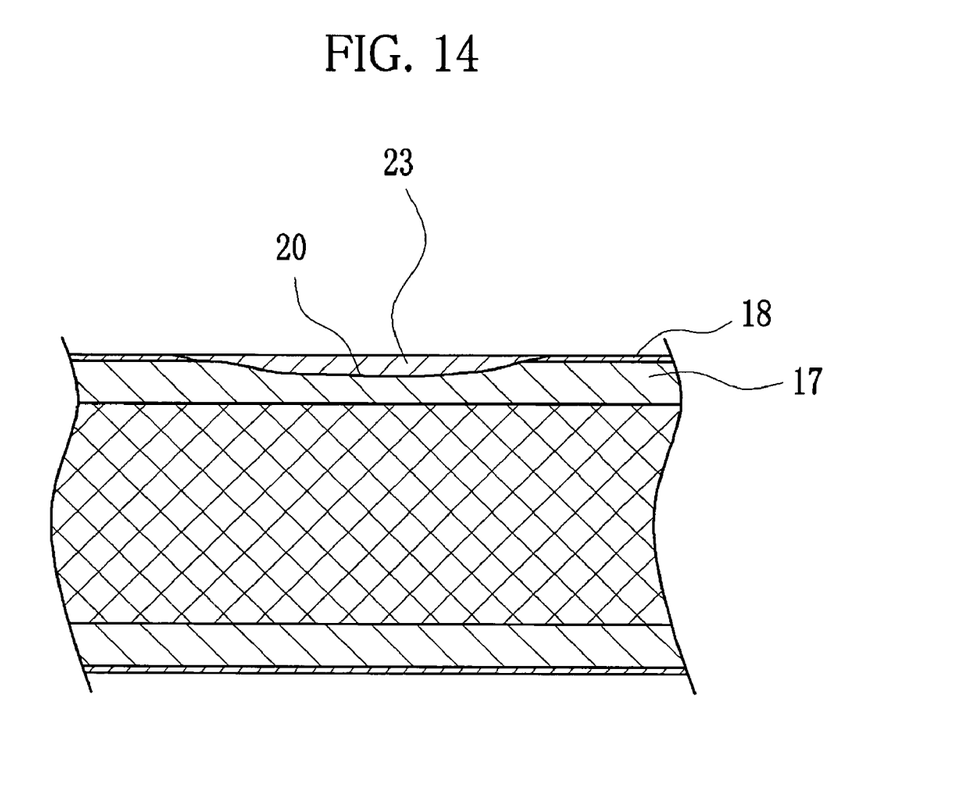
FIG. 14 is a cross-sectional view of the flexible tube from which the heat shrink tube has been peeled off.

As shown in FIG. 14, there are no surface irregularities between the surfaces of the repair material 23 and the jacket 15, that is, the surface of the repair material 23 is flush with the surface of the jacket 15. As a result, snagging of gauze on the repair material 23 does not occur even if the repaired flexible tube 10 is wiped with alcohol-soaked gauze for cleaning.

In the above embodiment, for the sake of easiness in covering the flexible tube, the heat shrink tube before shrinking or before heating has the inner diameter larger than the outer diameter of the flexible tube. Alternatively, for example, a rubber tube having the inner diameter equal to or slightly smaller than the outer diameter of the flexible tube may be used. In this case, the inner diameter of the rubber tube is expanded using a jig, for example, and then the flexible tube is inserted into the rubber tube. Thereafter, the jig is removed.

In the above embodiment, the main agent, acrylic polyol, of the repair material is the same as that contained in the top coat layer of the jacket of the flexible tube. However, the main agent of the repair material is not limited to it. To repair a jacket of a laparoscope, for example, epoxy polymer (prepolymer) may be used as the main agent of the repair material. The epoxy polymer is contained in an outer surface of angle rubber used in an angle section. An angle section of a laparoscope corresponds to a flexible tube of an endoscope. Alternatively, the main agent of the repair material may be silicone polymer which adheres to thermoplastic elastomer contained in the polymer layer. For example, a product of Shin-Etsu Chemical Co., Ltd., such as KE 445 (product name) may be used as the silicone polymer. To increase adhesion between the polymer layer and the repair material, a component that adheres to the polymer layer is added to the repair material.

In the above embodiment, to shorten the hardening time of the repair material, the flexible tube is placed on the electric hot plate and heated at a temperature in a range from 50° C. to 70° C. Alternatively, the repair material may be left in a room temperature and hardened without heating.

In the above embodiment, the pair of slits is formed in both end portions of the heat shrink tube. Alternatively, for example, one or more than three slits may be formed in each end portion. Such slits may be formed in at least one of the two end portions.

In addition, the heat shrink tube may be completely cut-open in its axial direction. In this case, the damaged area is covered with this cut-open tube, and then the cut-sides thereof are fastened with a heat-resistant adhesive tape. It should be noted that the polymer layer of the above embodiment may have a two-layer structure of, for example, a hard polymer and a soft polymer.

Although the present invention has been fully described by the way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A method for repairing a damaged area in a jacket of a flexible tube, said jacket being made from polymer, said method comprising:
   applying a liquid repair material to said damaged area;
   covering said damaged area with a repair tube and making a surface of said applied repair material flush with a surface of said jacket;
   hardening said repair material;
   peeling off said repair tube from said flexible tube; and
   peeling off at least a portion of the jacket around the damaged area,
   wherein said peeling off is conducted prior to the applying of the repair material.

2. The method of claim 1, wherein said repair tube comprises a material that is nonadhesive to said hardened repair material.

3. The method of claim 2, wherein said repair material contains a component adhesive to said jacket.

4. The method of claim 2, wherein said repair tube comprises a heat shrink tube that shrinks when heated.

5. The method of claim 4, wherein an inner diameter of said heat shrink tube before shrinking is slightly larger than an outer diameter of said jacket, and an inner diameter of said heat shrink tube after shrinking becomes smaller than said outer diameter.

6. The method of claim 4, wherein in said covering said damaged area, said heat shrink tube is heated and heat-shrunk after covering said damaged area.

7. The method of claim 2, wherein in said hardening said repair material, said repair material is heated at a temperature lower than a melting point of said jacket.

8. The method of claim 7, wherein said jacket comprises an inner layer and an outer layer.

9. The method of claim 8, wherein said repair material contains a same component contained in said outer layer.

10. The method of claim 8, further comprising peeling off at least a portion of the outer layer of the jacket around the damaged area.

11. The method of claim 1, wherein a slit is formed in each of end portions of said repair tube.

12. The method according to claim 1, further comprising sanding a portion of said jacket, which is exposed from said peeling off, into a gradual concave surface.

13. The method of claim 1, wherein the jacket is free from surface irregularities between a surface of the repair material and a surface of the jacket.

14. A method for repairing a damaged area in a jacket of a flexible tube, said jacket being made from polymer, said method comprising:
   applying a liquid repair material to said damaged area:
   covering said damaged area with a repair tube and making a surface of said applied repair material flush with a surface of said jacket;
   hardening said repair material;
   peeling off said repair tube from said flexible tube; and
   peeling off at least a portion of the jacket around the damaged area,
   wherein said peeling off is conducted using an adhesive tape.

* * * * *